1/20/84 US 4,483,343

United States Patent [19]

Beyer et al.

[11] Patent Number: 4,483,343

[45] Date of Patent: Nov. 20, 1984

[54] ULTRASONIC APPLICATOR

[75] Inventors: Johann Beyer, Baiersdorf; Walter Derndinger, Erlangen, both of Fed. Rep. of Germany

[73] Assignee: Siemens Aktiengesellschaft, Berlin & Munich, Fed. Rep. of Germany

[21] Appl. No.: 349,453

[22] Filed: Feb. 17, 1982

[30] Foreign Application Priority Data

Mar. 10, 1981 [DE] Fed. Rep. of Germany ....... 3109040

[51] Int. Cl.³ .............................................. A61B 10/00

[52] U.S. Cl. .................................................. 128/660

[58] Field of Search ................................ 128/660-661; 73/642, 644

[56] References Cited

U.S. PATENT DOCUMENTS

| | | | |
|---|---|---|---|
| 3,480,002 | 11/1969 | Flaherty et al. | 128/660 |
| 3,927,557 | 12/1975 | Viertl | 367/150 X |
| 4,059,098 | 11/1977 | Murdock | 128/660 |
| 4,163,394 | 8/1979 | Soldner . | |
| 4,208,602 | 6/1980 | Stoller | 128/660 X |
| 4,341,222 | 7/1982 | Gardineer et al. | 128/660 |
| 4,375,818 | 3/1983 | Sewaki et al. | 128/660 |

OTHER PUBLICATIONS

Knollman, G. C. et al., "Variable-Focus Liquid-Filled Hydroacoustic Lens", Jrnl. of Acoustic Soc. of America, vol. 49, No. 1, (PT2), pp. 253-255.

Taylor, W. B. et al., "A High-Resolution Transrectal Ultrasonographic System", UTS in Medicine & Biology, vol. 5, No. 2, pp. 129-138, (1979).

*Electromedica 46,* No. 4, 1978, pp. 141-148, Zurinski, V. and Haerten, R., "Real-Time-Sonographie mit dem Linear-Array-Scanner Multison 400", (Real-Time-Sonography with the Linear-Array-Scanner Multison 400).

"VIDOSON 735 SM, Ultraschall-Real-Time-Tomograph mit Wasservorlaufstrecke", (VIDOSON 735 SM, Ultrasound-Real-Time-Tomograph with Water Precursory Path), 1979, 6 pp.

*Primary Examiner*—Kyle L. Howell

*Assistant Examiner*—Francis J. Jaworski

*Attorney, Agent, or Firm*—Hill, Van Steadman & Simpson

[57] ABSTRACT

In an exemplary embodiment an ultrasonic head comprises at least one transducer element which, possibly via a liquid precursory path, transmits ultrasonic signals and receives echo signals. It is the object of the disclosure to design the applicator such that it is simply and rapidly adjustable to variable depth scanning. In accordance with the disclosure this object is achieved in that the liquid precursory path has the form of a sack, containing the liquid, which sack is capable of being coupled with the transducer element or elements on the ultrasonic head in the manner of a spacer by a readily detachable mounting arrangement.

6 Claims, 3 Drawing Figures

ULTRASONIC APPLICATOR

BACKGROUND OF THE INVENTION

The invention relates to an ultrasonic applicator comprising an ultrasonic head with transducer element means which transmits ultrasonic signals and receives echo signals.

In the human body the organs which are of interest in terms of an ultrasonic scanning, such as, for example, the kidneys, the thyroid gland, the liver, the heart and, in the case of women, also the female breast, respectively, lie at quite variable depths. In addition, these organs do not always exhibit an optimum position regarding the focus of the scanning ultrasonic beam. This applies in principle to all ultrasonic applicators with direct coupling to the body surface solely by way of a coupling gel. Such applicators are e.g. normal compound scanners, mechanical sector scanners and, in particular, also ultrasonic arrays in random design, such as are described e.g. in the article "Real Time Sonography with the Linear Array Scanner Multison 400" by V. Zurinski and R. Haerten in the publication "Electromedica" 46 (1978), No. 4, on pages 141 through 148. In addition, however, also such ultrasonic applicators are known in which the transducer elements are coupled to the body by way of a water precursory path. However, whereas the apparatus which is prior known from the brochure "VIDOSON 735 SM Ultrasonic Real Time Tomograph with Water Precursory Path DATA E 441" from the year 1979, does not render possible, without special measures, any variation of the distance of the transducer elements from the body surface, within the water precursory path, in the case of the ultrasonic array of U.S. Pat. No. 4,163,394, such a distance variation is possible. The last cited ultrasonic applicator relates specifically to a sector scanner which, on the basis of the curved design of the ultrasonic array, linearly scans in a sector. A displacement installation is provided which renders possible, within the water precursory path, an alteration of the distance between the curved array and the coupling location on the body. The location of the apex of the sector field in the interior of the body can hereby be varied to a certain extent with a simultaneous displacement of the entire sector field. The solution of U.S. Pat. No. 4,163,394 can be, at best, applied only to pure sector scanning, on the one hand. It is also relatively complicated, on the other hand, because an ultrasonic head with transducer elements must be arranged and displaced within a water bath in the housing of the ultrasonic applicator. A solution is desirable which is technically far simpler and, in addition, is also universally applicable to every type of ultrasonic applicator of the type referred to above.

SUMMARY OF THE INVENTION

It is the object of the invention to provide an ultrasonic applicator of the type referred to in the preceding section such that, along the lines of the preceding statements, it is simply and rapidly adjustable to variable depth scanning.

The object is achieved in accordance with the invention in that coupling means for providing a liquid precursory path, comprises a sack containing the liquid, which sack is capable of being selectively applied to the transducer element means of the ultrasonic head in the manner of a spacer, and readily detachable mounting means for detachably mounting said sack with said transducer element means.

The invention makes it possible for a liquid sack (with e.g. water or an oil which is a good conductor of ultrasound, or the like) to be connected with the ultrasonic head, which liquid sack flexibly varies the distance between sound-generating transducer elements of the ultrasonic head and the body surface, as a consequence of which, in turn, the scanning depth is altered. The liquid sack can be installed in the simplest fashion and it can likewise rapidly be dismantled again if a changeover is to be made from the scanning of skin-proximate regions (e.g. thyroid gland, kidneys, female breasts) to the scanning of deep-lying organs (e.g. liver, intestine or even heart). In the latter instance, direct coupling then again takes place with omission of the liquid sack. In a preferred embodiment of the invention, the liquid sack can be alterable in its dimensions by means of variably strong inflation, so that an additional depth variation is hereby rendered possible in the case of utilization of such a sack.

Further advantages and details of the invention are apparent from the following description of the exemplary embodiment on the basis of the accompanying drawing sheet in conjunction with the subclaims; and other objects, features and advantages will be apparent from this detailed disclosure and from the appended claims.

DETAILED DESCRIPTION

Figure 1:
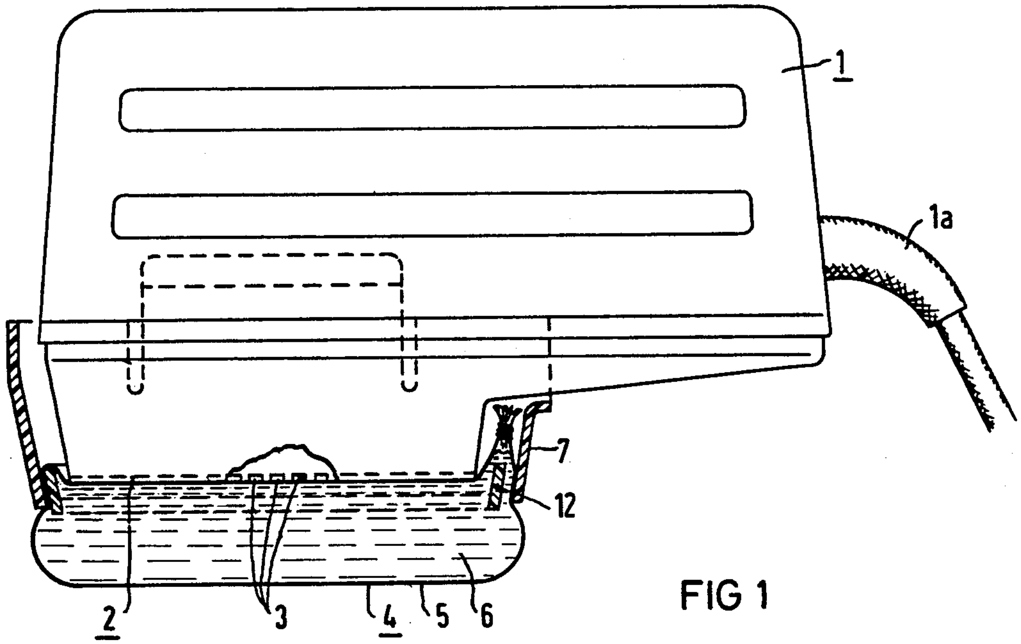
FIG. 1 illustrates an ultrasonic applicator according to the invention in a design as an ultrasonic array with a liquid sack connected with the sonic head, in lateral view, with certain applicator parts in section.
Figure 2:
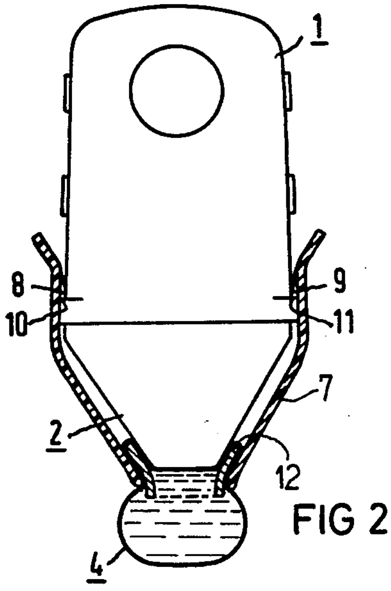
FIG. 2 illustrates the applicator of FIG. 1 in a frontal view again with the certain applicator parts in section.

In FIGS. 1 and 2, the ultrasonic array in the form of an ultrasonic applicator is referenced with 1. The ultrasonic array exhibits a connection 1a for an electric signal and energy supply-cable. The actual ultrasonic head is referenced with 2. It comprises on the application side a plurality of adjacently arranged transducer elements 3.

A liquid sack 4 is connected at the application side of the ultrasonic head 2 directly adjacent the transducer elements 3. The liquid sack 4 consists of a casing 5 of expandible material; e.g. natural rubber, which is filled with a liquid 6 having the property of being a good conductor of the ultrasound, particularly water or a corresponding oil, which liquid is additionally prepared specifically against fungus infestation with a special agent. The liquid sack 4 is clamped on the ultrasonic head 2 of the applicator 1 by means of a simple clamping part 7 which has the form illustrated in FIG. 1. The clamping part consisting of e.g. springy plastic material, e.g. hard-PVC (Astralon-T-UL), exhibits for this purpose two snap wedges 8 and 9 which, upon application of the liquid sack together with the clamping part on the applicator, snap into engagement with one shoulder flange 10 or 11 each at the periphery of the applicator housing. Thus, the liquid sack can be rapidly installed, on the one hand; however, it can just as simply and rapidly be removed from the applicator again due to the fact that the clamping part 7 with its snap wedges 8, 9, is readily removed from the shoulder flanges 10, 11, of the applicator.

Figure 3:
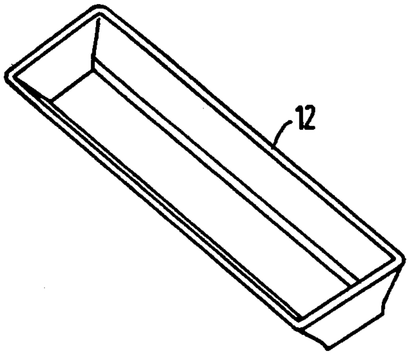
FIG. 3 illustrates an insert element for the liquid sack.

The water sack itself can exhibit varying dimensions corresponding to varying application conditions. In the case of one and the same array of transducer elements 3, the liquid sack, through correspondingly variably strong water inflation, can be alterable in its dimensions within certain boundaries, so that an additional depth variation in utilizing such a sack is hereby rendered possible. Serving the purpose of inserting the respective sack 4 in the clamping part 7 is an open frame or retainer 12, e.g likewise consisting of plastic, which exhibits the shape illustrated in FIG. 3. The frame 12 is respectively arranged in the interior of the liquid sack 4 such as indicated e.g. in FIGS. 1 and 2.

The liquid sack 4, which is coupled with the transducer elements 3 of the sonic head, serves as a flexible spacer; depending upon its dimensions, it varies the depth in which the focus of the scanning beam of the ultrasonic head 2 comes to lie. In the case of the connected liquid sack 4, above all, organs in the skin-proximate region can thus be scanned. If a switch is to be made to scanning of deeper lying organs, the sack 4 is again removed and the ultrasonic head 2 with the transducer elements 3 is directly coupled (solely via coupling gel) to the body surface.

It will be apparent that many modifications and variations may be effected without departing from the scope of the novel concepts and teachings of the present invention.

By way of example, the casing 5 may be of elastic material having initial dimensions when filled with liquid but not stretched, and having an initial interior liquid-receiving space when in the filled but unstretched condition, corresponding to an initial or minimum liquid capacity. By filling the casing 5 with a substantially larger amount of liquid than that corresponding to said minimum liquid capacity, the volume of the liquid-receiving space of casing 5 may be increased by at least ten percent, say by thirty percent without essentially exceeding the elastic limit of the material of the casing 5. In this way, the length of the water precursory path may be increased by at least ten percent in comparison to an initial length with the casing 5 filled but unstretched. Thus, during operation, the water precursory path may have any desired value over a substantial range of adjustment of at least ten percent.

We claim as our invention:

1. An ultrasonic applicator system comprising
(a) an ultrasonic head with transducer element means which transmits ultrasonic signals to and receives echo signals from a body under examination, said transducer head having an application surface for applying said transducer head to a body surface of said body under examination when ultrasonic signals are to be transmitted into comparatively deep-lying regions of said body,
(b) ultrasound coupling means providing a liquid precursory path between said application surface and said body surface when ultrasonic signals are to be transmitted into comparatively nearer regions of said body, said coupling means comprising
(b1) a sack containing a liquid, said sack comprising a completely closed casing of expandible material providing for a flexible coupling with said body surface, said casing being filled with said liquid, and
(b2) mounting means for readily and detachably mounting said filled sack as a unit on the ultrasonic head, said sack having an outer wall portion engaged in intimate contact with said application surface of said transducer head when said sack is mounted on said ultrasonic head, said sack thereby being capable of being selectively applied to the ultrasonic head in the manner of an elastic spacer, and said sack allowing for flexibly varying the distance between said transducer element means and said body surface, thereby altering the scanning depth in said body.

2. An ultrasonic applicator system comprising
(a) an ultrasonic head with transducer element means which transmits ultrasonic signals to and receives echo signals from a body under examination, said transducer head having an application surface for applying said transducer head to a body surface of said body under examination when ultrasonic signals are to be transmitted into comparatively deep-lying regions of said body,
(b) ultrasound coupling means providing a liquid precursory path between said application surface and said body surface when ultrasonic signals are to be transmitted into comparatively nearer regions of said body, said coupling means comprising
(b1) a sack containing a liquid, said sack comprising a completely closed casing of expandible material providing for a flexible coupling with said body surface, said casing being filled with said liquid, and
(b2) mounting means for readily and detachably mounting said filled sack as a unit on the ultrasonic head, said sack thereby being capable of being selectively applied to the ultrasonic head in the manner of an elastic spacer, and said sack allowing for flexibly varying the distance between said transducer element means and said body surface, thereby altering the scanning depth in said body, wherein said mounting means for mounting the liquid sack on the ultrasonic head comprises a clamping part including at least two snap wedges, which, during application of the liquid sack on the ultrasonic head, snap into detachable engagement with the periphery of the ultrasonic head.

3. The ultrasonic applicator system according to claim 2, wherein the clamping part is fabricated from springy plastic material.

4. The ultrasonic applicator system according to claim 3, with said clamping part being fabricated from polyvinyl chloride springy plastic material.

5. The ultrasonic applicator system according to claim 2, wherein said sack has a retainer means for holding the liquid sack in the clamping part which retainer means is arranged in the interior of the liquid sack.

6. The ultrasonic applicator system according to claim 5, with said retainer means comprising an open frame of plastic, said clamping part being of springy plastic material with an open end with minimum dimensions less than maximum dimensions of said open frame such that the open frame is supported against the perimeter of said head while being clear of the ultrasonic signals of the transducer element means.

* * * * *